US007516739B2

(12) United States Patent
Smith et al.

(10) Patent No.: US 7,516,739 B2
(45) Date of Patent: Apr. 14, 2009

(54) APPARATUS FOR DELIVERING PRESSURIZED FLUID

(76) Inventors: Lee Smith, 177 Riverside Ave., Apt. F1053, Newport Beach, CA (US) 92663; Robert A. Zarate, 23599 Red Oak La., Murrieta, CA (US) 92562

(*) Notice: Subject to any disclaimer, the term of this patent is extended or adjusted under 35 U.S.C. 154(b) by 215 days.

(21) Appl. No.: 11/406,078

(22) Filed: Apr. 18, 2006

(65) Prior Publication Data

US 2007/0006880 A1 Jan. 11, 2007

Related U.S. Application Data

(62) Division of application No. 10/439,368, filed on May 16, 2003, now Pat. No. 7,028,553.

(51) Int. Cl.
*A61M 15/00* (2006.01)

(52) U.S. Cl. ................................................ 128/202.26

(58) Field of Classification Search .................. 73/756; 128/202.19, 202.26
See application file for complete search history.

(56) References Cited

U.S. PATENT DOCUMENTS

| | | | | |
|---|---|---|---|---|
| 4,793,491 | A | 12/1988 | Wolf et al. | |
| 5,025,943 | A | 6/1991 | Forsman | |
| 5,822,838 | A | 10/1998 | Seal et al. | |
| 6,074,595 | A | 6/2000 | Eisberg et al. | |
| 6,082,408 | A | 7/2000 | Werling et al. | |
| 6,193,917 | B1 | 2/2001 | DeLay | |
| 6,311,738 | B1 | 11/2001 | Mason | |
| 6,405,882 | B1 | 6/2002 | Baxter | |
| 6,488,056 | B2 | 12/2002 | Mason | |
| 6,494,405 | B1 | 12/2002 | Kirn et al. | |
| 6,510,849 | B1 | 1/2003 | Izuchukwu et al. | |
| 6,691,702 | B2 * | 2/2004 | Appel et al. | 128/202.26 |
| 6,764,534 | B2 | 7/2004 | McCombs et al. | |
| 6,932,364 | B2 | 8/2005 | Koronowski et al. | |
| 7,028,553 | B2 | 4/2006 | Smith et al. | |
| 2002/0104860 | A1 | 8/2002 | Warner | |
| 2003/0005928 | A1 * | 1/2003 | Appel et al. | 128/202.26 |

OTHER PUBLICATIONS

Dawson, Douglas J., "Composite Cylinder Blast Overpressure Testing", Proceedings of the Twenty-Eighth Annual symposium Safe Association, San Antonio, Texas, Dec. 11-13, 1990. pp. 111-114.
Cal Plastic and Metals, Product information on "MONEL Alloy 400"; Apr. 4, 2003. <www://calplasticsandmetals.com/monel.html>.
Cal Plastic and Metals, Product Information on "Naval Brass, Naval Bronze-S.A.E. CA 464"; Apr. 4, 2003. <www://calplasticsandmetals.com/naval bronze.html.>.
ASTM STP 1267: "Flammability and Sensitivity or Materials in an Oxygen Rich Environment"; vol. 7. pp. 48-49, Tables 8-9.
Single page advertisement on "Expeditionary-Deployable Oxygen Concentration System E-DOCS-120" by Pacific Consolidated Industries.

* cited by examiner

*Primary Examiner*—Andre J Allen
(74) *Attorney, Agent, or Firm*—Knobbe Martens Olson & Bear LLP

(57) ABSTRACT

A container for enclosing at least one pressure vessel includes interface devices accessible on an exterior of the outer surface of the container. The container can also include various features for enhanced efficiency and convenience in stock piling of such containers.

28 Claims, 10 Drawing Sheets

APPARATUS FOR DELIVERING PRESSURIZED FLUID

RELATED APPLICATION

This application is a Divisional of U.S. application Ser. No. 10/439,368, filed May 16, 2003 now U.S. Pat. No. 7,028,553, which is incorporated herein by reference.

BACKGROUND OF THE INVENTION

1. Field of the Invention

The present application is directed to methods and devices for delivering pressurized fluids, and in particular, containers for enclosing pressurized fluid vessels.

2. Description of the Related Art

In the art of transporting pressurized fluids, it has long been known that a high level of volumetric efficiency is achieved where fluids are compressed into a liquid state. However, the storage of liquidized gases presents certain difficulties. For example, many fluids which are gasses at atmospheric conditions, require cryogenic storage conditions. As soon as such a liquidized fluid is removed from the cryogenic environment, it will continuously boil, thereby converting the liquid into gas. As such, the pressure within the vessel containing the liquid will rise, unless the gas generated by boiling is vented. The venting of such gas presents a loss of the fluid.

Until recently, most tanks used for transporting pressurized fluids have been made of steel or other metals. Recently, composite tanks have become commercially available. Such composite tanks typically are formed from a metal liner in a cylindrical shape and a lightweight reinforcing member on the outer surface of the liner. As such, the inner metal liner material provides a proper barrier for containing pressurized fluid and the outer material provides the added strength necessary for overcoming the radial expansion of the liner caused by the pressurized fluid. By using modern, lightweight composite materials for the outer reinforcing member, the overall weight of the pressure vessel is greatly reduced compared to the weight of conventional steel cylinders.

SUMMARY OF THE INVENTION

One aspect of at least one of the inventions disclosed herein includes the realization that modern lightweight composite compressed fluid cylinders can be grouped together to form a single portable fluid delivery device. For example, a plurality of lightweight compressed fluid cylinders can be housed together in a single container and connected with fluid delivery conduits to at least one output port disposed on an outer surface of the container. As such, the capacity of the compressed fluid vessels can be combined so as to increase the available fluid from a single package.

Thus, in accordance with another aspect of at least one of the inventions disclosed herein, a compressed fluid delivery system assembly comprises a housing, and a plurality of compressed fluid vessels are disposed in the housing. At least one fluid conduit connects the vessels to an outlet port disposed on an outer surface of the housing. As such, the capacity of the fluids can be combined to provide an increased capacity of a single unit.

Another aspect of at least one of the inventions disclosed herein includes the realization that in transporting a compressed fluid, it can be difficult to stock pile and transfer large numbers of compressed fluid vessels because such vessels are typically cylinder-shaped. For example, by housing at least one compressed fluid vessel in a container which includes projections and recesses configured to be nestable with each other, the housings can be stock piled or stacked conveniently in a stable manner. This further simplifies storing and transporting such fluid vessels.

Thus, in accordance with yet another aspect of at least one of the inventions disclosed herein, a compressed fluid housing assembly comprises a housing and at least one pressure vessel disposed therein. The housing includes a fluid outlet port disposed on an outer surface of the housing. Additionally, the housing includes projections and recesses that are sized so as to be nestable with each other. Thus, when a plurality of the housings are stacked, the projections and recesses nest with each other, thereby forming a more stable stack. This is particularly advantageous where such housings are transported in aircraft or other large vehicles, such as those commonly used in military operations.

Further aspects of at least one of the inventions disclosed herein includes the realization that where fluid ports are disposed on an outer surface of a housing containing pressurized fluid vessels, the ports can be damaged during transportation. Thus, in accordance with another aspect of at least one of the inventions disclosed herein, a fluid delivery assembly comprises a housing and a pressure vessel disposed therein. The housing includes at least one fluid outlet port disposed on the outer surface of the housing. The outer surface of the housing defines an outer peripheral contour. The outlet port is disposed in a recess such that the outlet port is recessed from the outer contour of the housing. As such, the outlet port is protected from impact or contact with other bodies.

Yet another aspect of at least one of the inventions disclosed herein includes the realization that where a pressure vessel is disposed within a housing of a fluid delivery unit, it can be difficult to determine the status of the pressure vessel if a plurality of the units are stacked. For example, if a number of fluid delivery units are stacked in adjacent stacks, a status indicator disposed on an outer surface of one of the units can be obscured by an adjacent stack. Thus, it can be advantageous if each housing includes a status indicator on two sides of the housing.

Thus, in accordance with yet another aspect of at least one of the inventions disclosed herein, a fluid delivery unit includes a housing and at least one pressure vessel disposed therein. The unit also includes two status indicators disposed on different sides of the outer surface of the housing.

As such, the user of such fluid delivery units has more flexibility in deciding how to stock pile the units. For example, having status indicators on two sides of the housing allows the user to choose between several alternatives for stacking the units so that at least one of the status indicator is visible when the units are stacked.

Another aspect of at least one of the inventions disclosed herein is that although storage of pressurized fluids in a gaseous state is less volumetrically efficient, certain pressurized gases can be stored more economically in a gaseous state, due to the elimination of losses associated with the storage of liquidized fluids.

For example, but without limitation, when liquid oxygen is stored in a non-cryogenic environment, the loses due to boiling are at least 2% per day and can be as high as 15% per day. Additionally, portable cryogenic equipment that can be used for transporting liquid oxygen, requires electric components. Such equipment can generate Electro-Magnetic Interference (EMI), which has resulted in restrictions against the use of such equipment on aircraft.

However, with the development of lightweight, high pressure vessels, large quantities of pressurized gaseous fluids, such as oxygen, can be stored indefinitely, with near zero loss, in a package that is comparable to the size and weight of a liquid oxygen container holding the same mass of oxygen. Thus, in accordance with yet another aspect of at least one of the inventions disclosed herein, a container for pressurized gaseous oxygen comprises a housing, at least one lightweight pressure vessel disposed in the housing. The pressure vessel is configured to store pressurized gaseous oxygen at a pressure of at least about 3,000 psi.

BRIEF DESCRIPTION OF THE DRAWINGS

These and other features, aspects, and advantages of the inventions disclosed herein are described below with reference to the drawings of a preferred embodiment, which is intended to illustrate and not to limit the invention. The drawings comprise the following figures.

DETAILED DESCRIPTION OF THE PREFERRED EMBODIMENT

Figure 1:
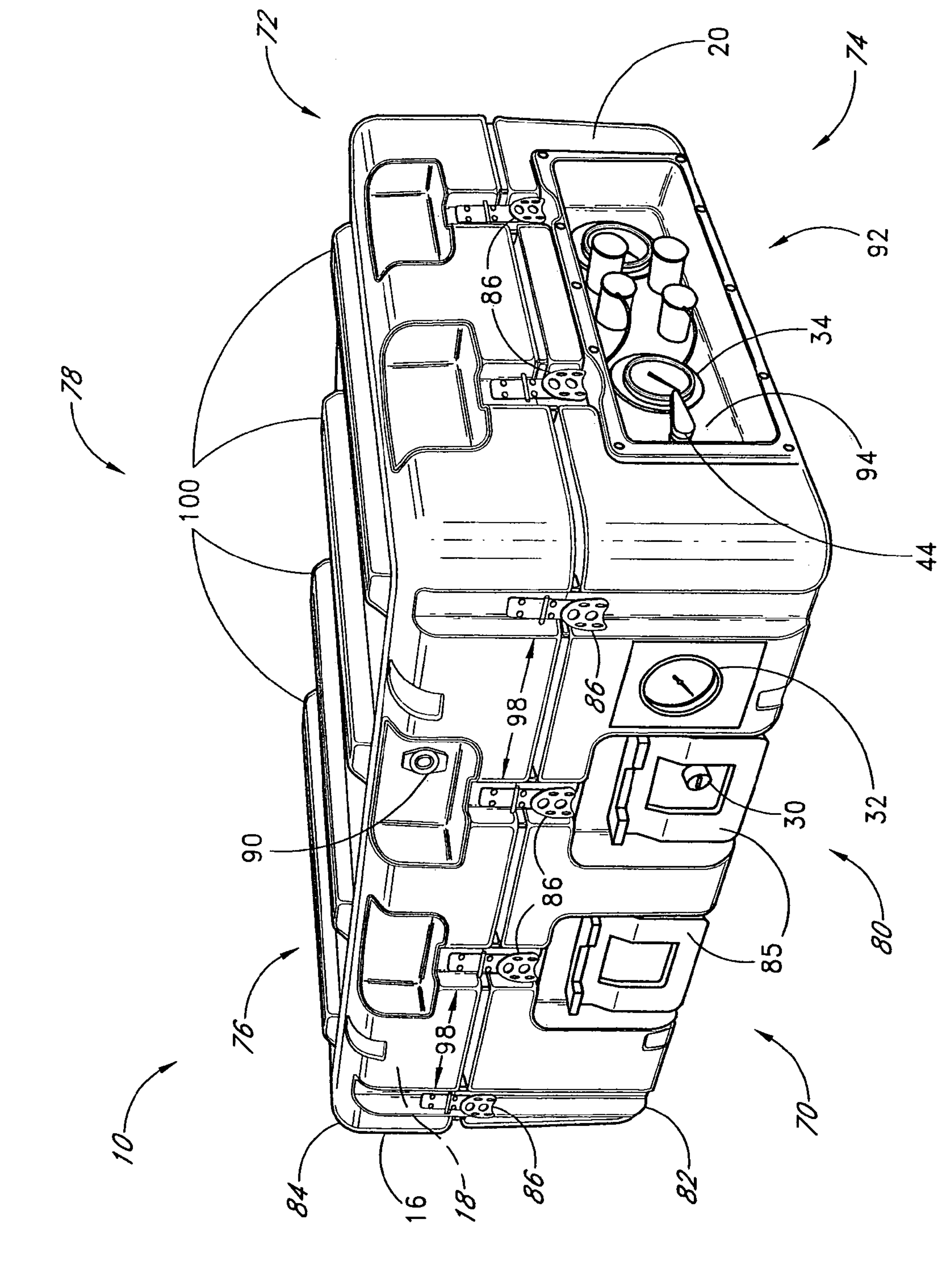
FIG. 1 is a top, front, and left-side perspective view of a pressurized fluid container constructed in accordance with an embodiment of a plurality of the inventions disclosed herein.
Figure 2:
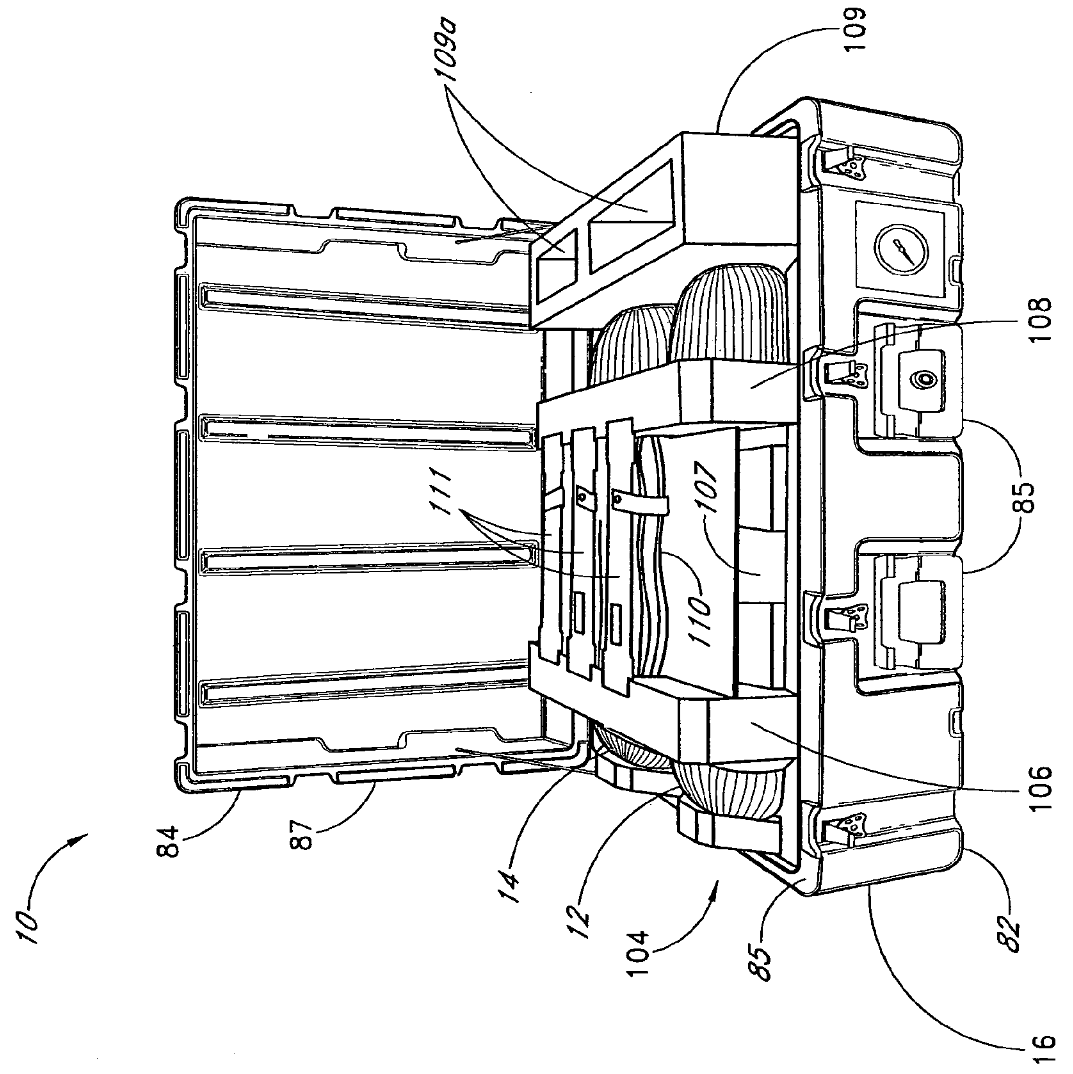
FIG. 2 is a front and top perspective view of the container illustrated in FIG. 1, in an open state and showing certain internal components including two pressurized fluid vessels.

With initial reference to FIGS. 1 and 2, a container 10 is illustrated therein. The container 10 is configured to enclose at least one pressure vessel, such as the pressure vessels 12 and 14 (FIG. 2). The container 10 includes a body 16 that defines an internal cavity 18 for containing the pressure vessels 12, 14. The body 16 also defines an outer surface 20 of the container 10. The outer surface 20 includes a plurality of recesses, described in greater detail below, for protecting certain devices disposed on the outer surface 20. The body can be constructed with any material. For example, but without limitation, the body 16 can be formed of metals, plastics, or composites. Preferably, the body 16 of the container 10 defines at least a substantially waterproof barrier for the internal volume 18. Further details of the body 16 are described below.

The pressure vessels 12, 14 can be of any known design. Preferably, the pressure vessels 12, 14 are in the form of light-weight composite pressure vessel. FIGS. 3-6 and the description set forth below, disclose different possible configurations for the vessels 12, 14. The description set forth below refers to only the vessel 12, because the container 10 can include one or a plurality of pressure vessels. Thus, in accordance with at least one of the inventions disclosed herein, the container 10 can include any type of pressure vessel, and any combination of the different containers described below.

Figure 3:
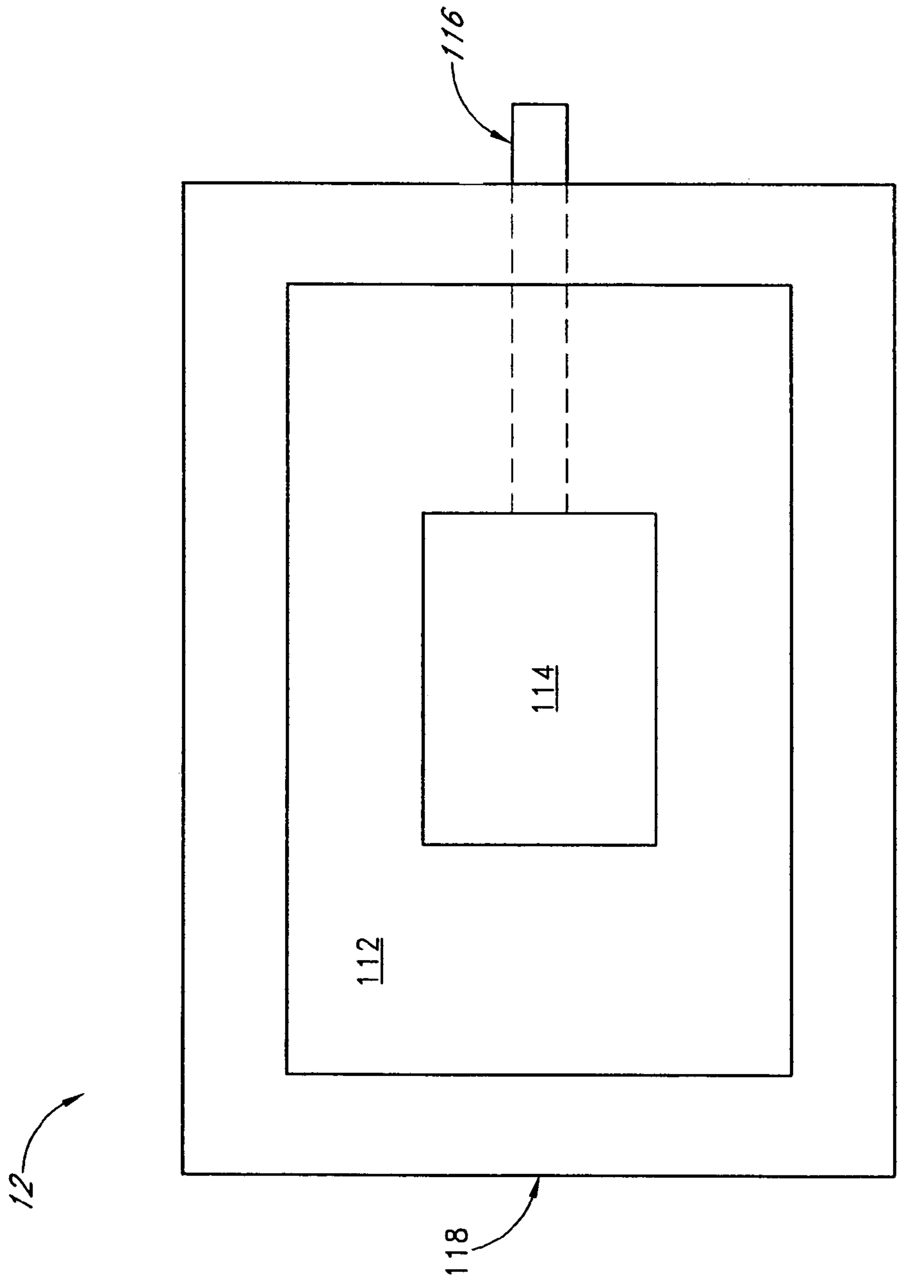
FIG. 3 is a schematic diagram of a pressure vessel having a copper alloy liner.

For example, with reference to FIG. 3, the pressure vessel 12 preferably includes a liner 112 formed of a material appropriate for creating a barrier for containing a pressurized fluid to be contained in the vessel 12. Where the fluid is oxygen, a copper or copper-based alloy material is preferred. As used herein, the term "copper-based alloy" is intended to include any alloy having at least a majority of copper. The liner 12 defines an internal cavity 14 which is configured to contain a pressurized fluid.

The liner 112 can define any shape. For example, the liner 112 can be in the shape of a cube, prism, sphere, cone or other conical shapes. Further, the liner 112 can be cast, machined, or manufactured from any form of stock material. For example, the liner 112 can be formed from sheet or plate material, and cut and/or bent into various shapes and welded together to provide a custom or non-standard shape. Of course, cylindrical shapes are most common.

The liner 112 can have any desired thickness. Generally, the thickness of the liner 112 would be determined by the desired rated maximum pressure of the pressure vessel 12 and the mechanical strength of the material used for the liner 112.

The pressure vessel 12 also includes a fitting 116 extending through the liner 112. Thus, the fitting 116 provides communication between the interior volume 114 and the exterior of the liner 112. The fitting 116 can have any known construction. For example, the fitting 116 can be in the shape of a tube, duct, or frustoconical conduit defining a fluid passage between the interior volume 114 and the exterior of the liner 112. Depending on the application, other devices, such as, for example, but without limitation, valves, gauges, filters, and regulators may be connected to the fitting 116.

The pressure vessel 12 also includes a second member 118 disposed around the liner 112. By constructing the pressure vessel 12 with a copper or copper-based alloy, and a second member 118 disposed around the liner 112, the pressure vessel 12 benefits from the low cost yet relatively inflammable characteristics of copper and copper-based alloys and benefits from the added strength of the second member 118. With the second member 118 disposed as such, the thickness of the liner 112 can be reduced, where the mechanical strength of the second member 118 carries the load caused by the radial expansion of the liner 112.

A further advantage is thus provided where the second member 118 is made from a material which has, or is configured to have a higher stiffness in radial expansion than the liner 112. When the internal volume 114 is filled with a pressurized fluid, the liner 112 will tend to expand against the second member 118. Thus, the second member 118 is configured to have or is made from material that has a higher stiffness or modulus of elasticity than the material forming the liner 112. Thus, when the liner 112 expands in response to a pressurized fluid within the internal cavity 114, the second member 118 will provide greater resistance against the radially outward expansion. Thus, the member 118 will carry more of the load created by the pressurized fluid in the internal volume 114 than the liner 112.

This configuration provides an additional advantage where copper or copper-based alloys are used for the liner 112. For example, copper and copper-based alloys, such as lead, tin, and yellow brasses, are generally weaker and softer than other materials that are known or considered to be materials that possibly can be used as liners for pressure vessels, such as, for example, aluminum and aluminum alloys, steel and steel alloys, and nickel and nickel alloys. Additionally, copper and copper-based alloys have a significantly higher density than aluminum and aluminum alloy which are commonly used as pressure vessel liners. Thus, by using a second member 118 having a greater resistance to radially outward expansion, the liner 112 can be made thinner and thus lighter, thereby limiting the total weight of the pressure vessel 12.

Figure 4:
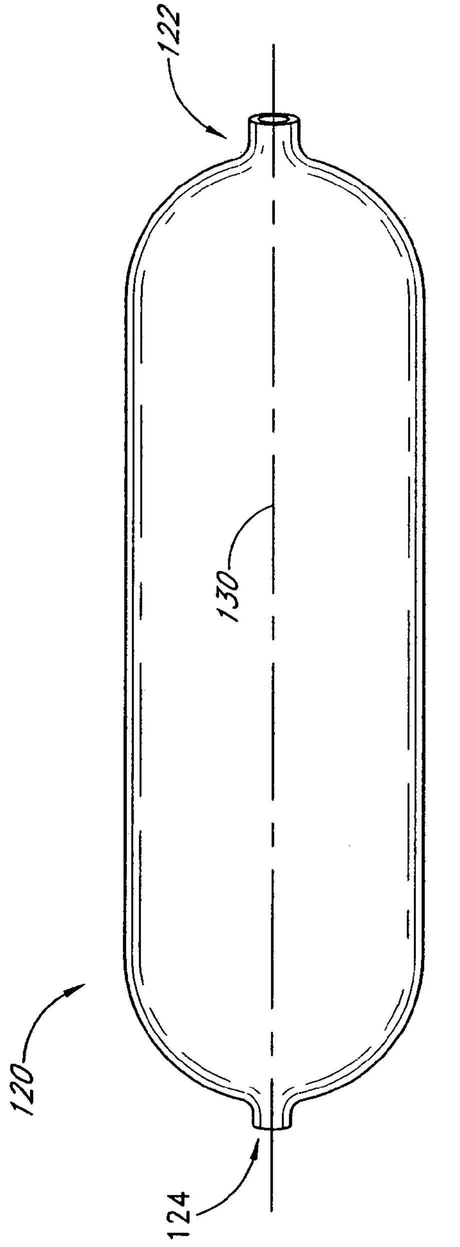
FIG. 4 is a side elevational view of a copper alloy liner of a pressure vessel.

FIG. 4 illustrates a modification of the liner 112, which is identified generally by the reference numeral 120. As noted above, with reference to the liner 112, the liner 120 is formed of a copper or copper-based alloy. The illustrated configuration of the liner 120 is an example of a configuration that is commonly used in the art of composite fluid tanks.

The illustrated configuration of the liner 120 is commonly referred to as a "mandrel." The mandrel is generally the shape of gas cylinders that have long been known in the art.

Preferably, the liner 120 has a fitting 122 at one end. Additionally, the liner 120 preferably has a boss 124 disposed at the end opposite the fitting 122. The boss 124 and the fitting 122 are used in a later step in manufacturing of a completed pressure vessel.

Preferably, as noted above, an outer member 128 is configured, or is made from a material, having a higher stiffness than the liner 120. Thus, the outer member 128 will carry a substantial portion of the load created by the radially outward expansion of the liner 120 caused by pressurized fluid being introduced into the internal cavity defined by the liner 120.

Figure 5:
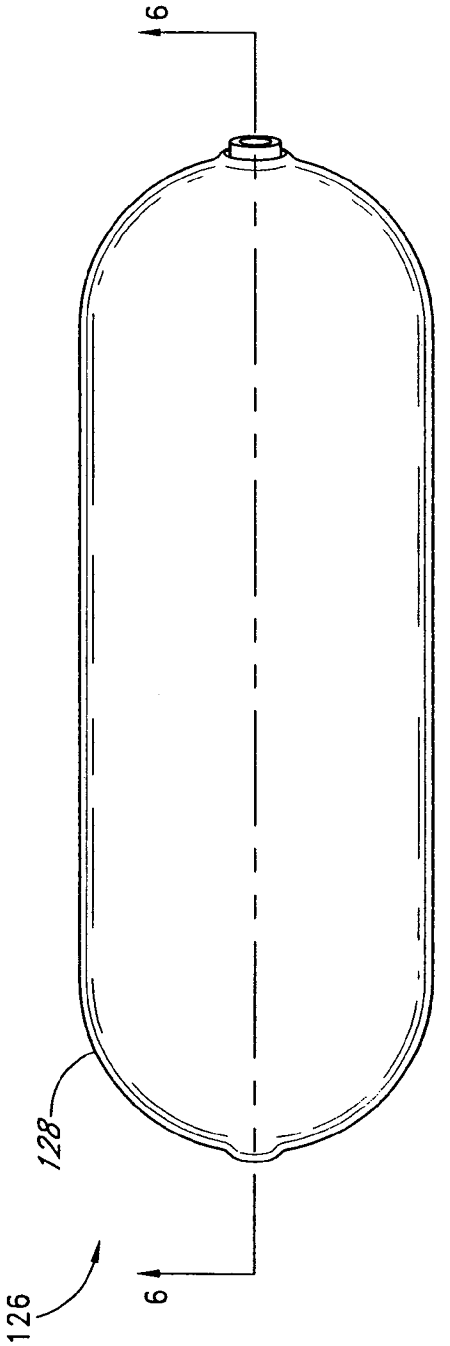
FIG. 5 is a side elevational view of a pressure vessel having the liner of FIG. 2 and a fiber reinforced material disposed around the outer surface of the liner.

For example, but without limitation, a fiber-based material such as a carbon fiber material can be disposed on the outer surface of the liner 120 to provide reinforcement therefor. FIG. 5 illustrates a completed pressure vessel 126 having a fiber-based material forming the outer member 128 which provides structural reinforcement for the liner 120. In the illustrated example, the material used for forming the outer member 128 is a carbon fiber material.

One method that is widely known for forming the outer member 128 as such, is to mount the liner 120, which is in the shape of a mandrel, to rotate about its longitudinal axis 130. As the liner 120 is rotated, a sheet of multi-directional carbon fiber fabric pre-impregnated with a resin is wrapped around the liner 120. However, other types of fiber-based materials or other non-fiber based material, as noted above, can be used to form the outer member 128. Other examples of fiber-based materials include, for example, but without limitation, fiberglass and Kevlar/epoxy. Additionally, the fiber material itself can be applied first, then a resin can be applied afterwards.

Depending on the material used, the outer member 128 may be subjected to further processes, such as for example, but without limitation, vacuum and heat treatments.

Figure 6:
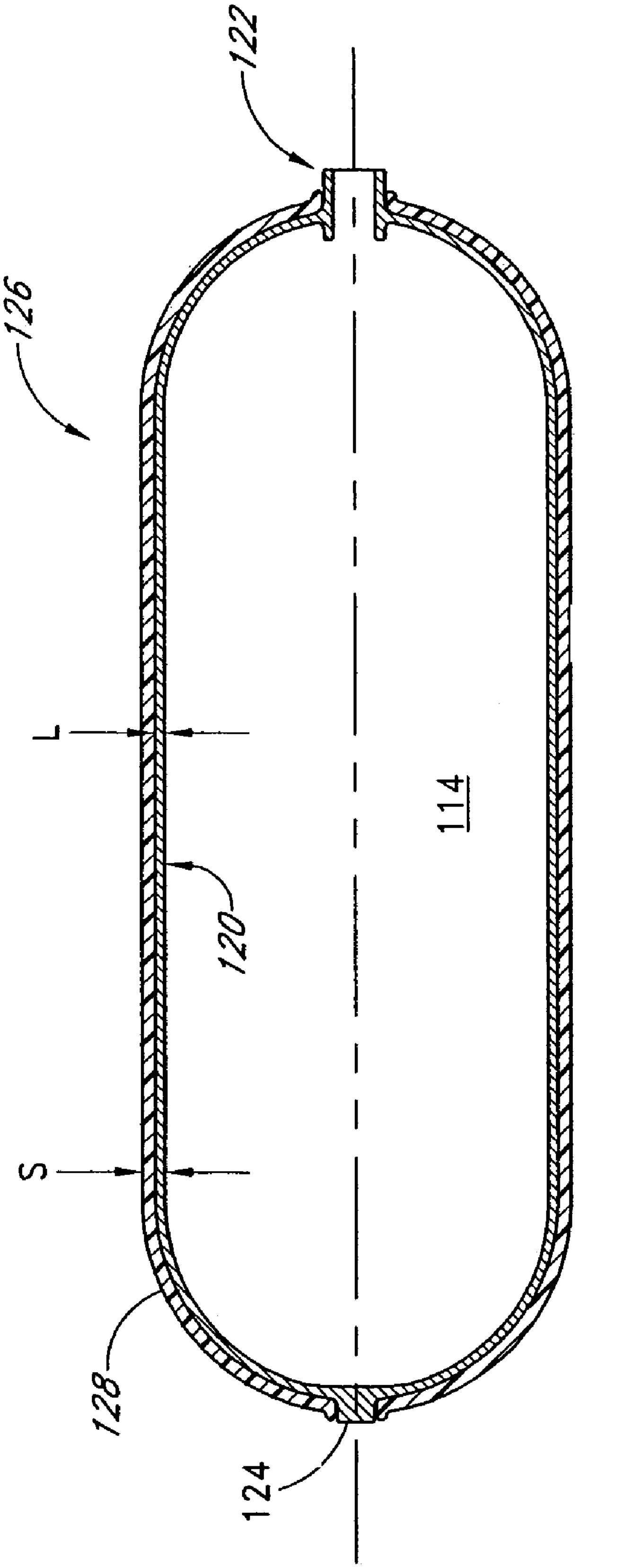
FIG. 6 is a sectional view of the pressure vessel shown in FIG. 3, taken along line 6-6.

FIG. 6 illustrates a sectional view of the pressure vessel 126 illustrated in FIG. 5. Preferably, the thickness L of the liner 120 is made as thin as possible, to minimize the weight of the liner 120. This is beneficial because, copper-based alloys have relatively high density, as compared to the density of aluminum. Thus, by minimizing the thickness L of the liner 120, the total weight of the pressure vessel 126 can be minimized.

Depending on the intended use of the pressure vessel 126, the thickness S of the outer member 128 is sufficiently large to support the liner 120 under the maximum load conditions. In an illustrative but non-limiting example, the internal volume 114 of the pressure vessel 126 is approximately 1.09 cubic feet. The overall length of the vessel 126 is approximately 29.4". In this illustrative example, the outer diameter of the pressure vessel 126 is approximately 10.15". Preferably, the liner has a thickness L between about 1/32 of an inch to about 1/4 of an inch. In this example, the thickness L of the liner 120 is approximately 0.062" and the thickness S of the second member is approximately 0.188". Preferably, the fitting 122 defines a standard 1/2" SAE port. As such, the pressure vessel 126 can be used with a variety of standard fluid handling fittings, valves, regulators, gauges, and filters.

In this configuration, the pressure vessel 126 would have a maximum rated pressure of about 3,000 psig. As such, the capacity of the pressure vessel, 126 is approximately 6700 standard liters of pure oxygen. These dimensions of materials will provide a proof pressure of about 4,800 psi and a design burst pressure of about 8,200 psi.

Copper and other copper-based alloys have a promoted combustion threshold pressure of about 7,000-8,000 psi in a pure oxygen environment. Thus, when the pressure vessel 126 is filled with pure oxygen to its maximum rated pressure of 3,000 psi, the pressure vessel 126 remains far more explosion resistant than compared to a similarly configured aluminum lined pressure vessel.

For example, aluminum and aluminum alloys such as aluminum 6061 and aluminum bronze have a promoted combustion threshold pressure of about 250 to 500 psi in a pure oxygen environment. Thus, a pressure vessel with an aluminum liner pressurized to 3,000 psi of pure oxygen would be highly flammable. If such a tank were punctured, the tank will be highly likely to burst into flames, with the aluminum itself becoming a fuel. However, when the tank 126, sized in accordance with the above-noted illustrative example, is filled with pressurized oxygen to approximately 3,000 psi, and if subjected to a strong mechanical impact such as by gunfire, the liner 120 could be deflected significantly without raising the pressure into the vicinity of the promoted combustion threshold pressure of copper or copper alloys in a pure oxygen environment. Thus, the pressure vessel 126 will not likely combust when subjected to such an event.

Additionally, because the liner 120 can be made generally thinner than the thickness that would be required if the entire vessel 126 was made from solid copper or copper alloy, the total weight of the pressure vessel 126 can be kept lower, thereby increasing and broadening the feasibility of using such a pressure vessel for transporting fluid such as gaseous oxygen.

Further, it is possible that, due to the lowered flammability of a pressure vessel such as the pressure vessels 12, 126, restrictions on the use of such pressure vessels will be reduced. For example, the reduced flammability of such pressure vessels may be sufficient to allow oxygen to be transported in military aircraft flying into combat zones. Thus, military field hospitals can be more easily supplied with gaseous oxygen for treating patients.

Figure 6A:
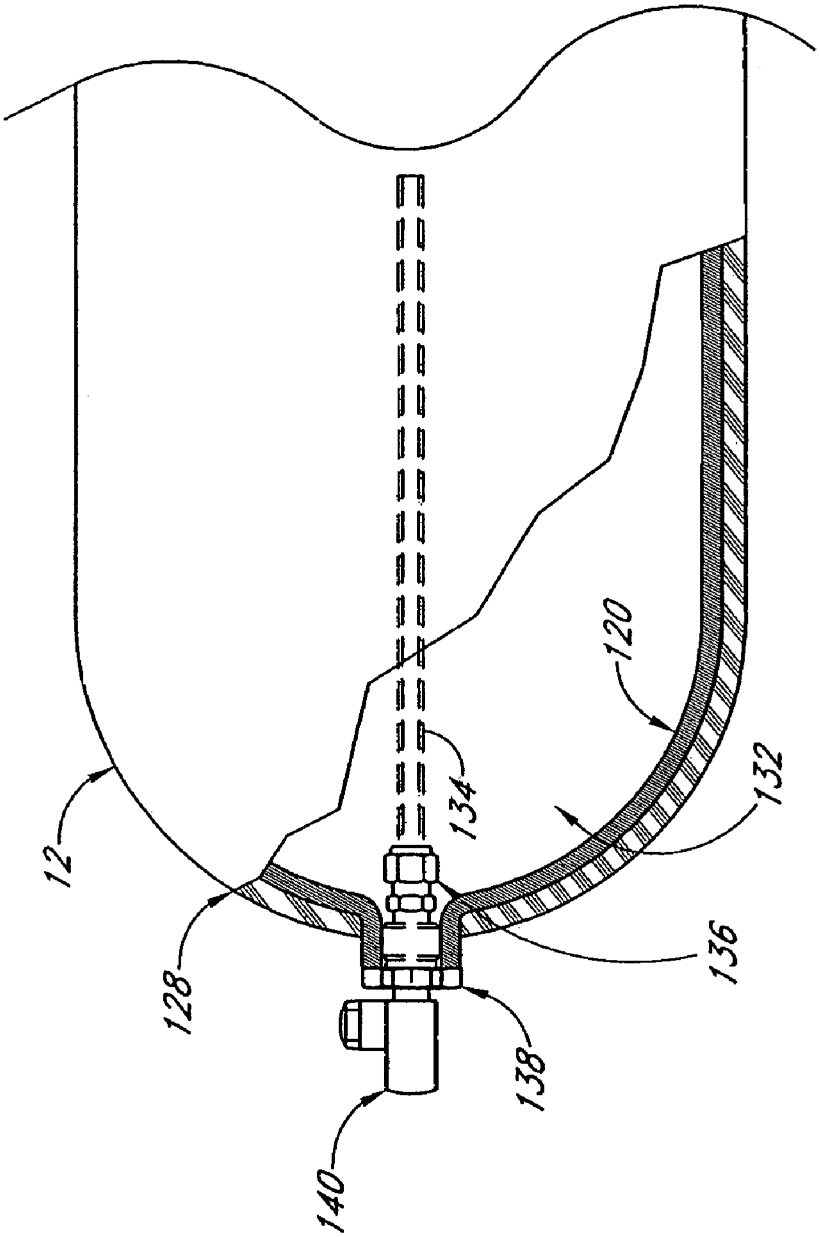
FIG. 6A is an enlarged sectional view of a modification of the pressure vessel shown in FIG. 6.

With reference to FIG. 6A, where the vessel 12 is to be used with a fluid delivery system described below with reference to FIG. 7, or other similar systems, the vessel 12 preferably includes a particle restriction device, such as the restriction device 132. In the illustrated embodiment, the restriction device is in the form of a perforated tube 132 extending from the fitting 122, into the interior 114 of the vessel 12.

The perforated tube 134 is mounted to the fitting portion 122 with a male connector 136 and a threaded fitting 138. A valve 140 can be connected to the threaded fitting 138. The perforated tube 134, male fitting 136, the threaded fitting 138, and the valve 140 are all commercially available, the use of which is well known in the art.

The perforated tube 134 includes perforation sized to prevent particles from passing out of the interior 114. As such, the tube 134 prevents particles that may be present in the interior 114 from clogging other equipment that can be connected to the vessel 12.

Exemplary Embodiment

Set forth below is a description of a further exemplary, but non-limiting, embodiment of a design for the vessels 12, 14. This exemplary embodiment is not intended to limit the inventions disclosed herein. Rather, the present exemplary embodiment is intended merely to illustrate one possible embodiment of at least one of the inventions disclosed herein. In particular, the exemplary embodiment described below has been developed to ease manufacturability and compliance with certain Department of Transportation (DOT) regulations.

In this exemplary, but non-limiting embodiment, the pressure vessel can be dimensioned as noted above with reference to the non-limiting, exemplary dimensions noted above with reference to the pressure vessel 126 illustrated in FIGS. 4-6. As such, the cylinder can be a seamless brass alloy liner wound with carbon fiber reinforced plastic composite layers and subjected to an autofrettage pressure. As such, the carbon filament impregnated with epoxy layers are the predominant pressure load bearing elements.

The vessel 126 can also include an outer layer consisting of glass filament impregnated with epoxy resin providing damage protection. The liner and the layers are configured such that the outer glass layer will carry less than 10 percent of the total pressure at the minimum required burst pressure.

The brass liner can also include a thin layer (approximately 0.010 inches) of an epoxy resin reinforced glass veil matt disposed on its outer surface to prevent galvanic corrosion. Together the inner and outer glass filament layers should carry less than 15 percent of the total pressure load at the minimum burst pressure.

The winding pattern of the carbon fiber reinforced plastic composite layers may be a combination of helical (including near longitudinal) and hoop. A layer made up of more than one type of fiber could be, but preferably is not used. The marked service pressure can be as high as 5000 PSI at a reference temperature of 70° F.

The test pressure is preferably 1.67 times the design service pressure. The cylinder should also have a safety factor (burst/service pressure ratio) of about 3.4. The service life of the vessel can be estimated at about 15 years from the date of manufacture.

The liner can be a cylinder made of 260 brass. The liner preferably has no more than one circumferential seam approximately at the midpoint of the cylindrical portion of the vessel. The liner can be constructed with a boss at the closed end, for ease of winding and a threaded boss at the open end. The bosses may be welded in place with a seam preferably no larger than 3 inches in diameter.

The materials composition of the brass are preferably within the ranges as follows:

| ELEMENT | MIN % | MAX % |
|---|---|---|
| COPPER | 68 | 72 |
| ZINC | 28 | 32 |
| OTHER | — | 0.5 |

The liner interior surface preferably is smooth. Any fold in the domed area due to the forming or spinning process preferably is not sharp, deep, or detrimental to the integrity of the liner. Inner surface defects can be removed by machining or another method. However, preferably the metal loss is minimal and the minimum required wall thickness is maintained. Additionally, the ends of the liner should be concave to pressure.

The mechanical properties of brass liner material preferably fall into the following ranges: yield strength 17K-29K psi, tensile strength 47K-70K psi, and elongation (2" gauge) at least 25%.

The, carbon fibers can be polyacrylonitrile (PAN) based carbon fiber tows. The tensile strength of these tows can be at least about 600,000 psi. The modulus of the elasticity preferably is from about 38 million psi to 46 million psi. Additionally, the strain to failure preferably is not be less than about 1 percent.

The glass fibers preferably are type E glass fibers. As noted above, the glass over-wrap can be used merely for abrasion protection and as a carrier for the green pigment.

The resin matrix systems can be an epoxy or a modified epoxy type having a pot life compatible with the filament winding process used. The resin matrix system selected preferably has sufficient ductility so that cracking of the resin matrix system does not occur during the manufacturing of the cylinder or during normal operation for the useful life of the cylinder.

The composite overwrap preferably is formed by layers of continuous fibers in a matrix. Helical or near longitudinal windings preferably cover the entire surface of the liner. When circumferential layers are interspersed for strengthening the side wall, physical discontinuity between the layers preferably is minimized. The fibers preferably are not comingled. Thus, each layer preferably contains only one type of fiber. However, the overwrap can be applied through wet winding or pre-impregnated filament winding.

The design and stress analysis of a carbon fiber reinforced pressure vessel can be complex because of the varying load bearing layers, the varying orientation and thickness of composite layers, and the potential that the liner is subjected to above yield strains at the time of an autofrettage pressure cycle.

Thus, a reliable model of the cylinder can be used in order to calculate the maximum stress at any point in the liner and fibers; and load distribution between liner and fibers at zero pressure, service pressure, test pressure, and burst pressure. For these purposes, the model used to analyze the cylinder body can be based on thin shell theory, account for non-linear material behavior and nonlinear geometric changes, and account for both circumferential and longitudinal pressure stresses. In such a design effort, the vessel body can be analyzed alone. However, maximum stresses in the cylinder ends should always be less than the maximum stresses in the vessel body to pass burst tests.

Such an analysis is most conveniently performed with finite element techniques to analyze the stresses in the fibers. Preferably, the maximum calculated tensile stress (at service pressure) in any fibers (carbon or glass) do not exceed 30 percent of the fiber stress corresponding to the minimum required burst pressure.

The maximum calculated tensile stress at any point in the liner at the service pressure preferably does not exceed 60 percent of the yield strength of the liner material. The compressive stress in the sidewall of the liner at zero pressure preferably is at least 60 percent and not more than 95 percent of the minimum yield strength of the liner material.

The maximum fiber stress at service pressure of the carbon fibers or glass fibers preferably does not exceed 30 percent of the fiber stress corresponding to the minimum required burst pressure. Additionally, the vessel preferably is configured such that in the burst failure mode, failure will start in the cylindrical side-wall portion of the vessel.

Preferably, openings are on heads only. Thus, the centerline of the openings preferably coincide with the centerline of the vessel.

Any threads on the liner preferably are clean cut, even, without checks, and designed in compliance with the requirements of the Federal Standard FED-STD-H28. Straight threads having at least 6 threads preferably have a calculated factor of safety in shear of at least 10 at the test pressure for the cylinder.

Figure 7:
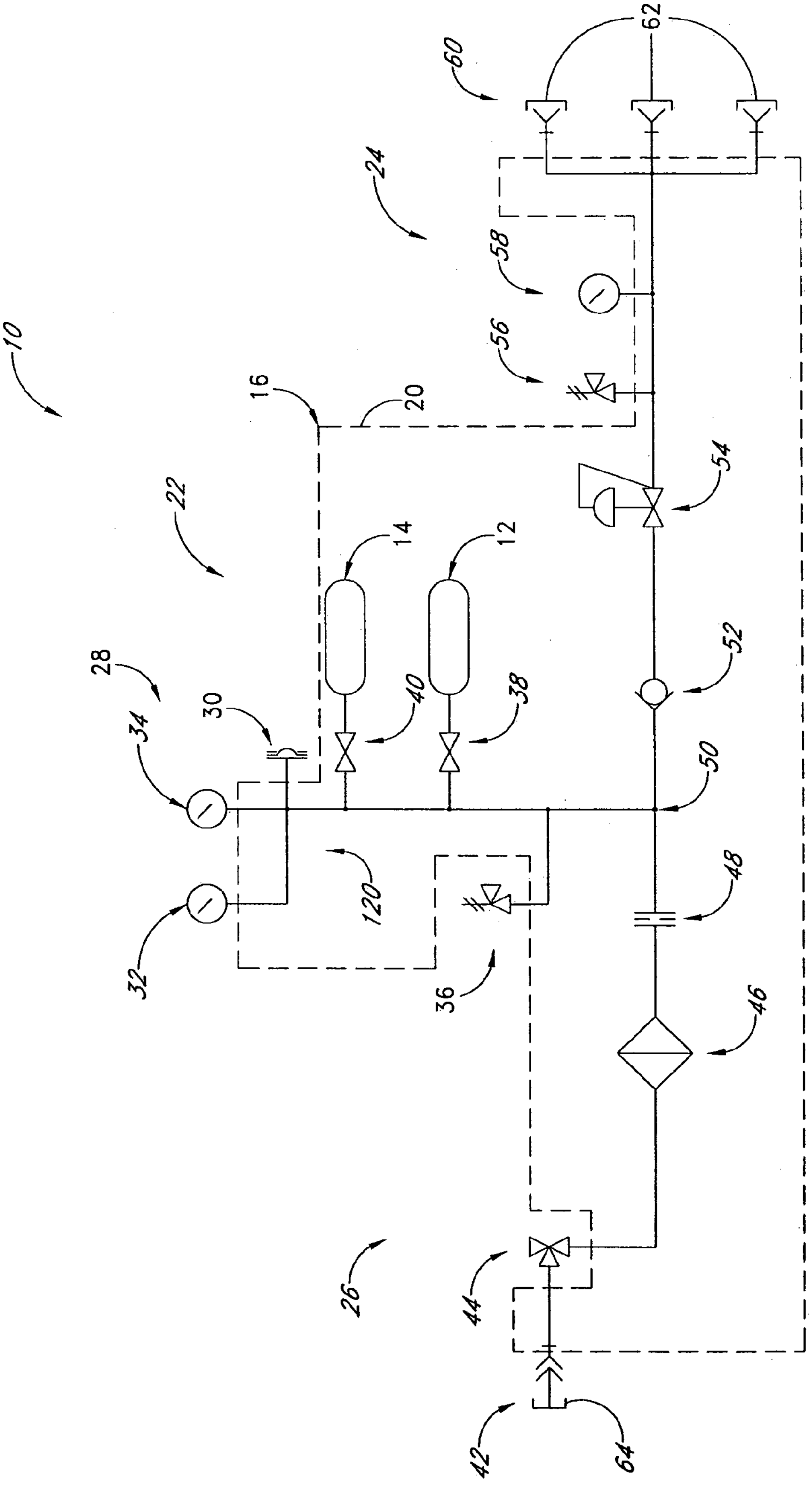
FIG. 7 is a schematic illustration of the container illustrated in FIGS. 1 and 2, illustrating the connections between the pressurized fluid vessels and certain other components including gauges disposed on an outer surface of the container.

With reference to FIG. 7, the connections of the various devices connected to the vessels 12, 14, are illustrated therein schematically. Generally, the container 10 includes a fluid storage portion 22, a fluid delivery portion 24, and a fluid refill portion 26. The fluid storage portion 22 includes at least one pressure vessel, such as one of the pressure vessels 12, 14. The fluid storage portion 22 can be configured to store any pressurized fluid in a gaseous or liquid state. In one exemplary embodiment, the fluid storage portion 22 is configured to store a purified gas, such as purified oxygen.

Preferably, the fluid storage portion 24 includes at least one status indicator 28 disposed so as to be viewable from an exterior of the container 10. Preferably, at least one status indicator 28 is configured to indicate status of at least one of the pressure vessels 12, 14, disposed in the container 20. In the illustrated embodiment, the status indicators include an over pressure sensor 30 and pressure gauges 32, 34.

The over pressure sensor 30 can be in the form of any known sensor configured to produce an output when a predetermined pressure has been exceeded. In the illustrated embodiment, the over pressure sensor 30 is a burst-disk indicator. Burst-disk type indicators are well known in the art and is commercially available. One commercially available burst-disk device is sold by Continental Disc Corp., as model S13.

In one exemplary, but non-limiting, embodiment, the burst-disk device is configured to be triggered at 4700 psi. Additionally, the burst-disk indicator is mounted to the body 16 such that if the burst-disk device has been triggered, a user can determine through visual inspection, that the storage portion 22 has been over pressurized. Such an over pressurization can occur, for example, if one of the tanks 12, 14 have been damaged, such as by impact, or if the container 10 has been heated to a point at which the pressure within the tanks 12, 14 is raised due to elevated temperature. As such, the over pressure sensor 30 is mounted so that a user of the container 10 can determine that the system has been over pressurized without having to move or open the container 10. Thus, the user of container 10 can take the appropriate safety precautions for handling the container 10 before attempting to move or open it.

The pressure gauges 32, 34 can be of any known type. Preferably, the pressure indicators 32, 34 are configured to have a maximum reading that is sufficiently high to provide accurate readings at any pressure that may be generated within the storage portion 22. In one exemplary, but not limiting embodiment, the gauges 32, 34 are configured to give pressure readings between zero and 5000 psi. Such pressure gauges are commercially available from the WIKA Instrument Corporation, model 9768xxx-CBM-FF.

The storage portion 22 also preferably includes a pressure relief valve 36. The pressure relief valve 36 is disposed so as to discharge fluid from a container 10 if the pressure in the tanks 12, 14 exceeds a predetermined threshold. In one exemplary embodiment, the pressure relief valve is configured to release the pressurized fluid to the atmosphere on the exterior of the outer surface 20 when the pressure in the storage portion 22 exceeds 3,220 psi. Such relief valves are commercially available from Nupro, as an R3A series relief valve.

Preferably, the container 10 also includes shut-off valves 38, 40 disposed at the outlets of the tanks 12, 14, respectively. The shut-off valve 38, 40 preferably include a manually operable knob for selectively connecting and disconnecting the tanks 12, 14 from the other components of the storage portion 22. In the illustrated embodiment, the shut-off valves 38, 40 are two position valves. Such valves are commercially available from the Swagelock Company, model SS-4P4T5. However, the illustrated valves 38, 40 are merely exemplary. Any type of valve can be used.

The various components of the storage portion 22 including the tanks 12, 14, the status indicator 28, including the over pressure sensor 30, and pressure gauges 32, 34, as well as the relief valve 36, and shut-off valves 38, 40, as well as the components (described below) of the delivery portion 24 and the filling portion 26, are connected using standard plumbing conduit commonly used in pressurized fluid systems. The specific plumbing conduits and connectors used depend on the type of pressurized fluid to be stored in the storage portion 22. Where the pressurized fluid is oxygen, the conduits connecting the various components of the storage portion 22 can be rigid or flexible. A flexible conduit is commercially available from the Swagelock Company, advertised as the TH Series Flex Hose, which is internally coated with Teflon (PTFE) and includes a braided stainless steel outer sheathing.

It is to be noted that the status indicators 28, and the relief valve 36 are schematically illustrated as being disposed on an exterior of the outer surface 20 of the container 10. However, as described in greater detail below, certain devices, such as the status indicators, need not be disposed on the exterior of the outer surface 20. Rather, the status indicators preferably are mounted merely to be visible from an exterior of the outer surface 20, thereby providing the additional advantage of allowing users to read these instruments without having to open the container 10. Additionally, it is to be noted that the shut-off valves 38 and 40 can be disposed so as to be operable from an exterior of the outer surface 20.

The filling portion 26 is configured to allow the storage portion 22 to be filled or refilled with a pressurized fluid. In the illustrated embodiment, the filling portion 26 includes an inlet port 42, a valve 44, a filter 46, and a restriction device 48.

The inlet port 42 preferably is mounted so as to be accessible from the exterior of the container 10. The port 42 can be in the form of any pressurized fluid port used for pressurized fluid delivery systems. Preferably, the inlet port 42 defines a quick-connect type connector. For example, in an exemplary but non-limiting embodiment, the inlet port 42 can be comprised of a connector assembly, commercially available from the Swagelock Company, as the QTM2 DESO Stem and QTM-2 Body.

The valve 44 is disposed downstream from the inlet port 42, in the direction of fluid flow into the storage portion 22. Preferably, the valve 44 is a three-way valve, selectively switchable between an open position, a closed position, and a vent position, described in greater detail below. Such a valve, as an exemplary embodiment, is commercially available from the Swagelock Company, as the Whitney "40" Series Ball Valve.

The filter 46 is disposed downstream from the valve 44. The filter 46 can be any type of filter used in pressurized fluid delivery systems. In the illustrated embodiment, the filter 46 is made from a sintered metal. In one exemplary embodiment, where the container 10 is configured for handling pure oxygen gas, the filter 46 is in the form of a sintered, stainless steel filter. Such a filter is commercially available from Nupro, as the SS-4TF-40 filter.

The restriction device 48 is disposed downstream from the filter 46. The restriction device 48 is configured to restrict a flow of fluid through the filling portion 26. The restriction device 48 is configured based on the performance desired for a particular application. For example, where the container 10 is used to store oxygen, the restriction device 48 preferably is configured to limit the flow through the filling portion 26 so as to limit the rate of increase of pressure in the system to about 200 psi per minute. For example, in one exemplary embodiment, the restriction device 48 is in a form of a restriction orifice having a diameter of approximately 0.047 inches. Such a restriction device is available from O'Keefe Controls Co., as the E-series orifice.

As illustrated in FIG. 3, the filling portion 26 is connected to the storage portion 22, schematically represented by a point 50, such that pressurized fluid entering the filling portion 26 passes to the pressure vessels 12, 14.

The discharge portion 24 includes check valve 52, a pressure regulation device 54, a relief valve 56, a pressure gauge 58, and at least one outlet port 60. The check valve 52 can be configured to prevent a flow of fluid from the discharge portion 24 toward the storage portion 22 or the filling portion 26. In the illustrated embodiment, the check valve 52 is also configured to retain a predetermined fluid pressure within the storage portion 22. For example, in the exemplary embodiment, the check valve 52 can be configured to have a threshold opening pressure of 25 psi, such that the valve 52 will not open unless the pressure on the upstream side is 25 psi higher than the pressure on the downstream side. Such a check valve is commercially available from Nupro, as a CH-Series—Stainless check valve.

The pressure reduction valve 54 is disposed downstream from the check valve 52. Preferably, the pressure reduction valve 54 is configured to reduce a pressure of a pressurized fluid from the storage portion 22 to a pressure no greater than about 55 psi, in an exemplary embodiment. Additionally, the pressure reduction valve 54 can be adjustable. For example, the pressure reduction valve 54 can be configured to allow a user to adjust the pressure output of the valve 54. Such a configuration can include an adjustment screw (not shown). The screw can be mounted on the interior or exterior of the container 10. Such a pressure reduction valve is commercially available from Victor Equipment as the SR250D-540 model.

The relief valve 56 is disposed downstream from the pressure reducer valve 54. Preferably, the pressure relief valve 56 is configured to relieve excessive pressure in the discharge portion 24. In an exemplary embodiment, the pressure relief valve 56 is configured to vent fluid from the discharge portion 24 if the fluid reaches a pressure greater than about 60 psi. Such a relief valve is commercially available from Nupro as the SS-8CPA2 or SS-4CPA2 relief valves.

The pressure gauge 54 is disposed downstream of the pressure relief valve 56. Preferably, the pressure gauge 58 is disposed so as to be visible from an exterior of the outer surface 20.

Finally, the outlet ports 60 are disposed downstream from the pressure gauge 58. In the illustrated embodiment, there are three outlet ports 60. However, any number of outlet ports can be provided. In an exemplary embodiment, the outlet ports 60 can be Schraeder quick connect fittings, model no. 69-201-34.

When filling the container 10, for example, when the pressure vessels 12, 14, are empty or have only about 25 psi of fluid stored therein, the valve 44 is first placed in the "vent" position. Additionally, one should ensure that the shut-off valves 38 and 40 are in the open position. Then, a pressurized fluid supply is connected to the input port 42. Initially, the supply should be in the off position while the conduit is connected to the input port 42.

After the supply is connected to the input port 42, the valve 44 is moved to the open position. At this point, the supply of the pressurized fluid should be introduced slowly. Additionally, the fill rate of fluid being introduced into the container 10 should not exceed about 200 psi per minute. Preferably, the restriction device 48, as noted above, is configured so as to limit the fill rate to about 200 psi per minute where the pressurized fluid is oxygen.

The container 10 can be filled until the design pressure is reached. For example, in an exemplary embodiment, the pressure vessels 12, 14 have a design pressure of about 3000 psi. Thus, when the pressure vessels 12, 14 are filled to 3000 psi, the supply to the filling portion 26 should be stopped.

After the supply to the refilled portion 26 is stopped, the valve 44 should be moved to the vent position which will thereby allow some of the fluid to bleed out of the filling portion 26. The supply device should then be disconnected from the input port 42. The valve 44 can then be moved to the close position.

When using the container 10 as a pressurized fluid supply, the user should first select the proper flow regulator. The flow regulator chosen should first be set to a closed position. Then, the flow regulator can be connected to one of the outlet ports 60. Once the flow regulator is connected to one of the outlet ports 60, the user should check to ensure that the output pressure gauge 58 indicates that the output pressure is about 50 psi±5 psi, in the exemplary embodiment where oxygen is the pressurized fluid.

At this point, further interface equipment should then be connected to the flow regulator. When any of the ports 60, 42 are not in use, covers such as the covers 62 and 64 should be connected to the ports 60, 42, respectively.

With reference to FIG. 1, the body 16 includes the front side 70, a rear side 72 (not shown in FIG. 1), a left side 74, a right side 76 (not shown in FIG. 1), a top 78 and a bottom 80 (not shown in FIG. 1). It is to be noted that the sides 70, 72, 74, 76, 78, and 80 have been labeled as such for convenience only. The indication of front, rear, left, right, etc. has been chosen arbitrarily to ease the description set forth herein. It is to be understood that the container 10 can be used in a variety of orientations which would be contrary to the labels noted above.

In the illustrated embodiment, the body 16 is comprised of a lower portion 82 and an upper portion 84. The lower and upper portions 82, 84 are hinged relative to one another along the back side 72 of the body 16. Thus, the lower and upper portions 82, 84 can be rotated relative to each other between a closed position (FIG. 1) and an open position (FIG. 2). However, hinges (not shown) can be disposed on any side of the container 10. Additionally, the body 16 can be divided into parts having other shapes that allow access into the internal cavity 18. In the illustrated embodiment, handles 85 are disposed on the lower portion 82.

The lower portion 82 and the upper portion 84 include cooperating surfaces 85, 87, respectively. The cooperating surfaces 85, 87 are configured to engage with each other so as to provide a generally weather-proof seal therebetween. Optionally, the surfaces 85, 87 can be configured to form substantially watertight or airtight seals when the surfaces 85, 87 are engaged with each other.

The container 10 also includes a plurality of locks 86 disposed along the outer periphery of the body 16. Preferably, the locks 86 are configured to generate tension when in a locked position, so as to seal the surfaces 85, 87 against each other. If desired, a gasket can be provided between the surfaces 85, 87 so as to further enhance the sealing engagement of the surfaces 85, 87.

Preferably, the container 10 also includes an atmospheric vent 90. The vents 90 can be configured to allow a pressure build up of air or fluid within a container 10 to be vented to the atmosphere when the pressure of such air or fluid exceeds the predetermined threshold. Further, the atmosphere vent 90 can be configured to also act as a one-way valve. Thus, the vent 90 will allow fluids to escape from the interior volume 18 but prevent fluids from entering interior volume 18.

Figure 8:
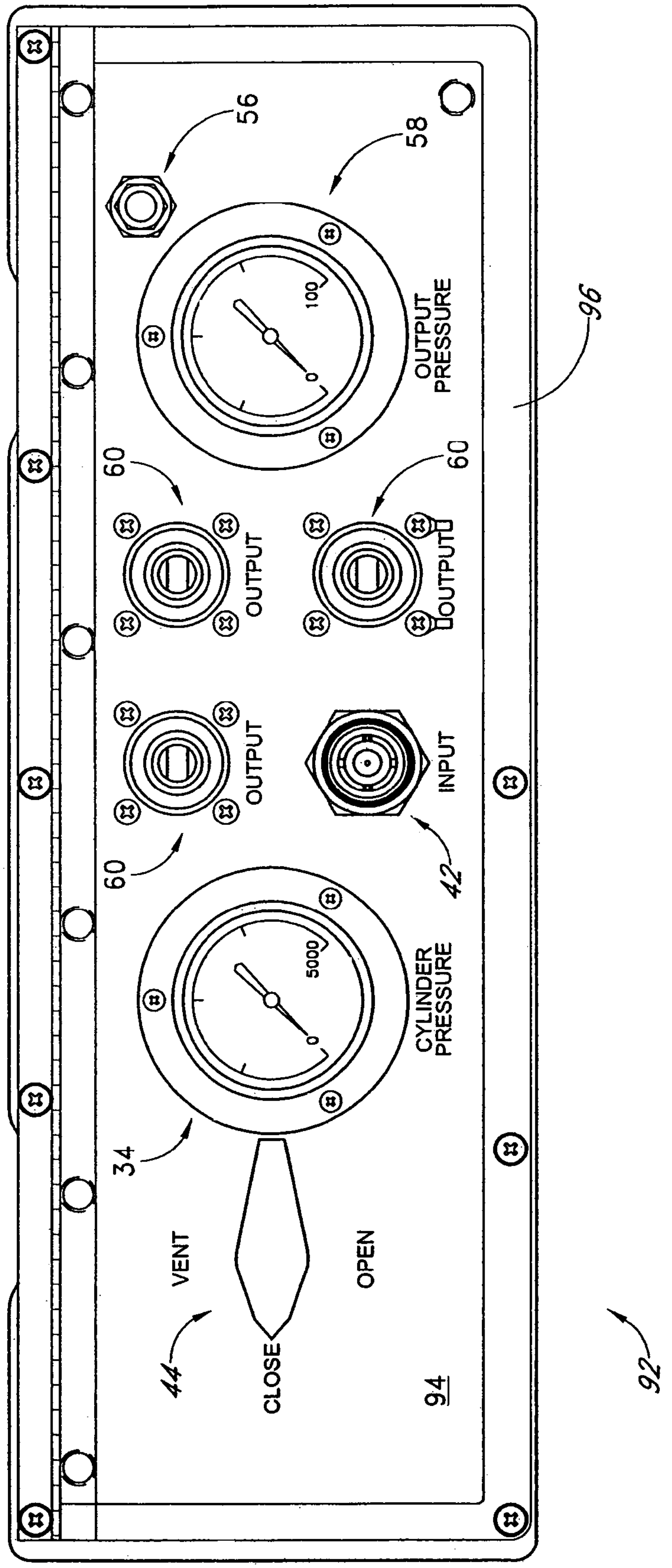
FIG. 8 is an enlarged left-side elevational view of a gauge panel disposed on an outer surface of the container illustrated in FIG. 1.
Figure 9:
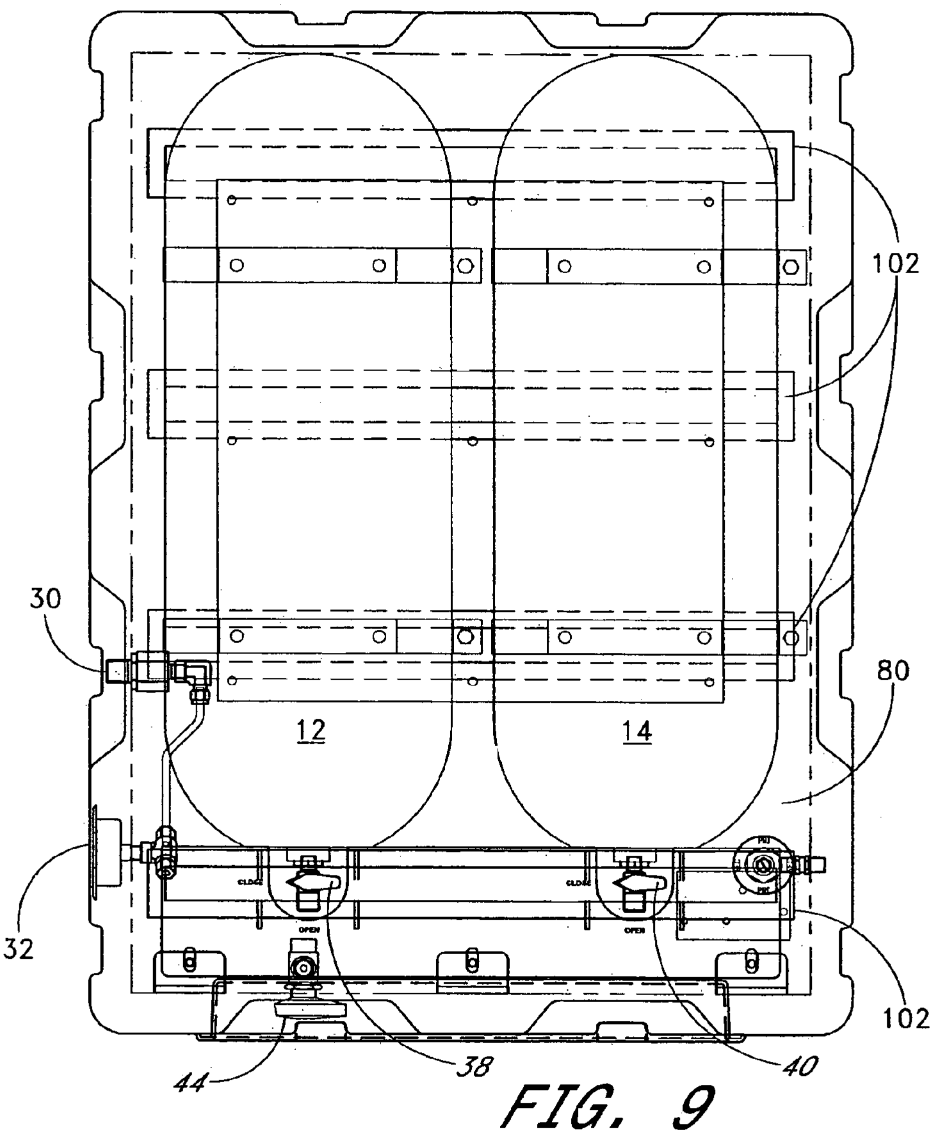
FIG. 9 is a top plan view of the container illustrated in FIG. 1, with certain internal components also illustrated.
Figure 10:
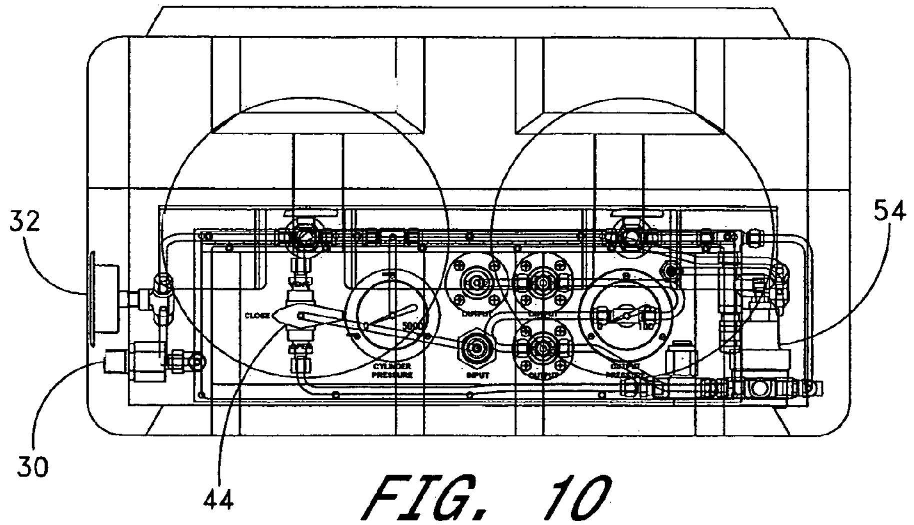
FIG. 10 is a left-side elevational view of the container illustrated in FIG. 1, with certain internal components also illustrated.
Figure 11:
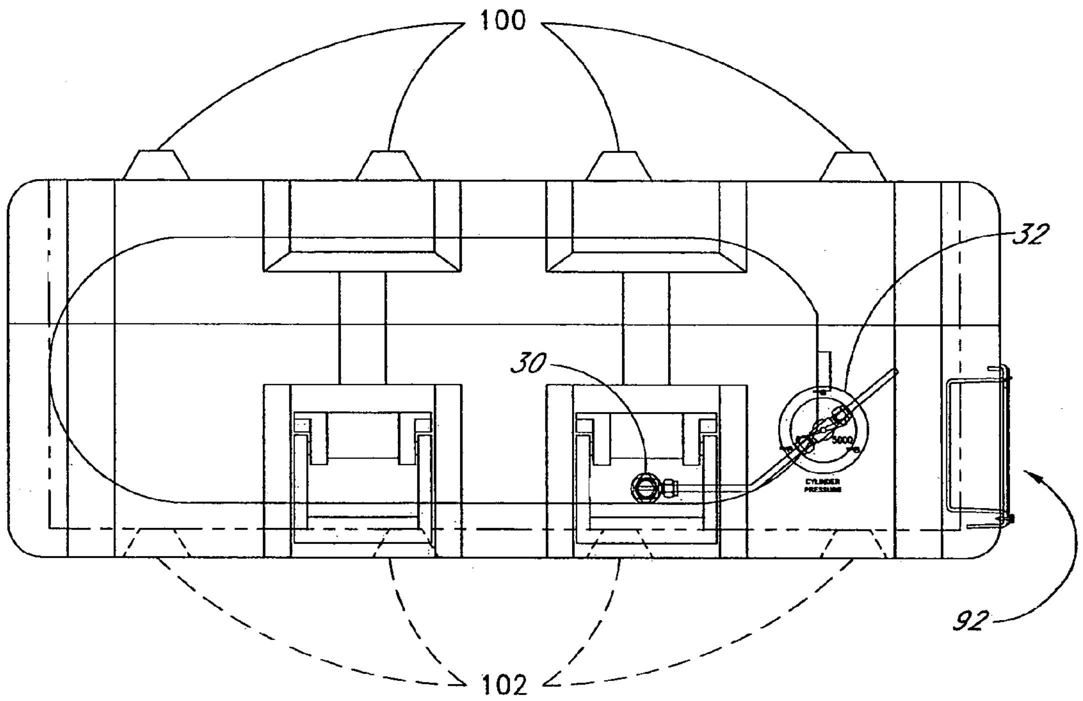
FIG. 11 is a front-side elevational view of the container illustrated in FIG. 1, with certain internal components also illustrated.
Figure 12:
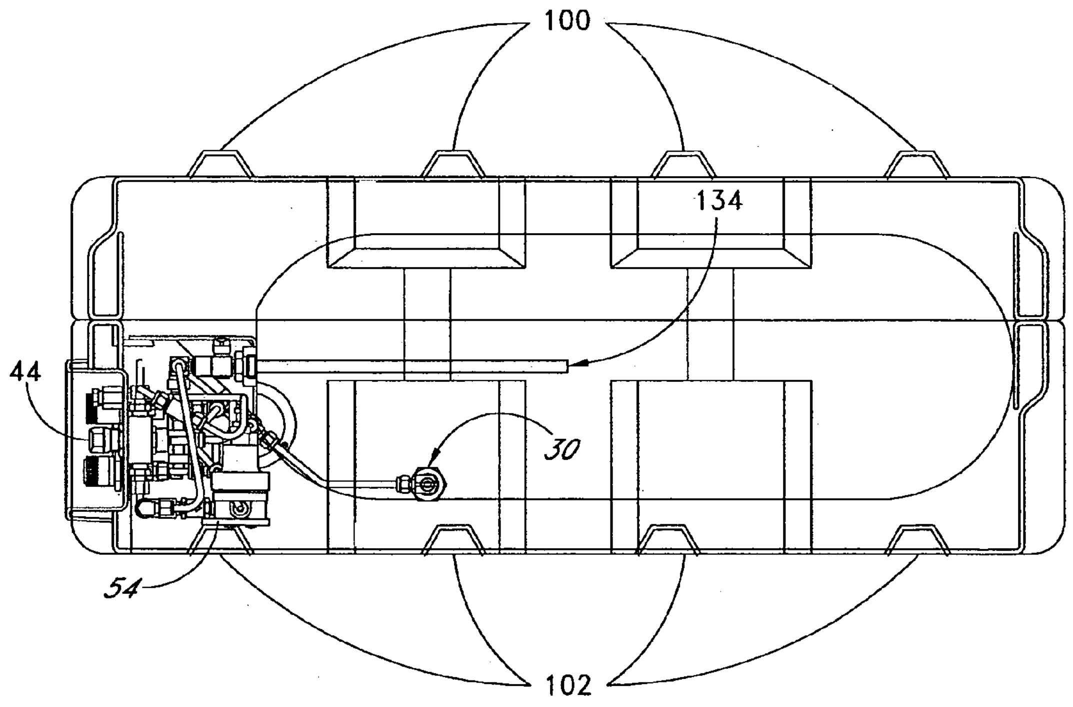
FIG. 12 is a rear elevational and partial cut away view of the container illustrated in FIG. 1.

With reference to FIG. 1, the container 10 contains a gauge panel 92 disposed on the left side 74 of the container 10. With reference to FIG. 8, the gauge panel 92 includes a mounting surface 94 configured to receive at least one of the devices illustrated in FIG. 7 as being disposed on the exterior surface 20 of the container 10. In the illustrated embodiment, the gauge panel 92 provides mounting positions for the valve 44, the pressure gauge 34, the outlet ports 60, the input port 42, the output pressure gauge 58, and the relief valve 56.

Optionally, as illustrated in FIG. 8, the gauge panel 92 can include a dust cover 96. In the illustrated embodiment, the dust cover 96 is made from a sheet of metal. The cover 96 latches to secure it to the gauge panel 92. Thus, the cover 96 can be closed during storage. However, when the container 10 is being used as a pressurized fluid delivery device, the cover 96 can be removed so that the ports 60, 42 and the valve 44 can be accessed.

As shown on FIG. 1, the mounting panel and thus the devices 34, 42, 44, 56, 58, and 60 are recessed from the outer surface 20 of the container 10. Thus, when the container 10 is being transported or stacked, the devices 34, 42, 44, 56, 58, and 60 are protected from being damaged by impact with other bodies.

Similarly, the outer surface 20 includes additional recesses 98 in which the locks 86 are disposed. As such, the locks 86 are protected from impact with other bodies. Thus, the locks are less likely to be damaged if the container 10 comes into contact with other bodies or is placed on the ground such that any of the sides 70, 72, 74, 76 are resting on the ground. Additionally, the locks 86 are also less likely to inflict damage on other articles.

As shown on FIG. 1, the gauge 32 is disposed on the front side 70 of the container 10. By arranging the pressure vessel pressure gauges 32, 34 on different sides of the container 10, a further advantage is provided in that when a plurality of containers 10 are stacked upon each other or otherwise stored in a confined area, it is easier for the user to visually determine if the pressure vessels 12, 14 within the container 10 have any remaining pressurized fluid stored therein.

As shown in FIG. 1, the upper side 78 of the container 10 includes a plurality of projections 100. In the illustrated embodiment, the projections 100 are generally rib shaped and extend parallel to one another and generally in the direction from the rear side 72 toward the front side 70. However, the projections 100 can be of any shape.

As shown in FIG. 5, the bottom surface 80 of the container 10 includes a plurality of recesses 102. The recesses 102 are shaped in size to correspond to the projections 100. Additionally, the projections 100 are aligned to the recesses 102, as illustrated in FIGS. 7 and 8. Advantageously, the projections 100 and the recesses 102 are configured to be nestable with each other. Thus, when a container 10 is stacked upon another container having projections 100, the recesses 102 of the container 10 nest with the projections 100 of the lower container. As such, the container 10 can be stacked in a more stable manner, thereby allowing the container 10 to be stacked more quickly and safely.

With reference to FIG. 2, preferably, cushions 104 are disposed around the pressure vessels 12, 14, so as to provide further protection against damage. The cushions can be made from any conventional material used for cushioning articles, such as, for example, but without limitation, air bladders, expanded foam, etc.

In the illustrated embodiment, the cushions 104 include transverse portions 106, 107, 108, and 109. The transverse portions 106, 107, 108, and 109 each extend across both of the vessels 12, 14, however, these portions could be of any size or shape. Advantageously, the certain of the cushions 104 includes recesses for securing accessories that can be used in conjunction with the container 10. For example, in the illustrated embodiment, the transverse portions 106, 108 include recesses for securing fluid conduits 110. The fluid conduits 110 can be disposed in the recesses, or they can be strapped to boards 111, which are received in the recesses. Additionally, the portion 109 includes recesses 109*a* which can be used to store other accessories for use with any of the devices carried by the container 10.

Of course, the foregoing description is that of preferred arrangements having certain features, aspects and advantages in accordance with various combinations of the inventions disclosed herein. Various changes and modifications may be made to the above-described arrangements without departing from the spirit and scope of the inventions, as defined by the appended claims.

What is claimed is:

1. A portable oxygen delivery system comprising a housing and a plurality of tanks disposed within the housing and configured to store pressurized gaseous oxygen, a plurality of output ports disposed on a first outer surface of the housing, a regulator connecting the plurality of tanks with the plurality of the output ports such that oxygen from any of the plurality of tanks can be discharged through any of the output ports, at least a first gauge disposed adjacent to the plurality of the output ports, the first gauge being of a first type of pressurized fluid gauge, a second gauge disposed on a second side of the housing, the second gauge being of the first type, a plurality of grooves being disposed on a lower surface of the housing and a corresponding plurality of projections disposed on an upper surface of the housing such that when a plurality of housings are stacked on top of each other, corresponding grooves and projections nest with each other thereby stabilizing the stack of housings.

2. The system according to claim 1, wherein the plurality of tanks comprise a metal liner and a lightweight composite covering over the liner.

3. A container for transporting a pressurized fluid comprising a housing and at least a first pressure vessel disposed within the housing, the housing comprising a first outer surface having a plurality of projections and a second outer surface, opposite the first surface, the second surface comprising a plurality of recesses corresponding to the plurality of projections, the projections and recesses being configured so as to the nestable with each other, and at least one input port disposed on the outer surface of the housing and connected to the pressure vessel so as to allow the pressure vessel to be refilled with a pressurized fluid.

4. The container according to claim 3 additionally comprising at least a second pressure vessel disposed within the housing.

5. The container according to claim 3 additionally comprising at least one fluid output port disposed on outer surface of the housing, the at least one fluid output port being connected to first pressure vessel.

6. The container according to claim 5 additionally comprising at least a second pressure vessel, the output port being connected to both the first and second pressure vessels so as to receive pressurized fluid from both the first and second pressure vessels.

7. A container for transporting a pressurized fluid comprising a housing and at least a first pressure vessel disposed within the housing, the housing comprising a first outer surface having a plurality of projections and a second outer surface, opposite the first surface, the second surface comprising a plurality of recesses corresponding to the plurality of projections, the projections and recesses being configured as to the nestable with each other, and a first pressure gauge disposed on a third surface of the housing and a second pressure gauge disposed on a fourth surface of the housing.

8. The container according to claim 3 additionally comprising at least one of a gauge, knob, and port disposed in a recess of an outer surface of the housing, such that the at least one of a gauge, knob, and port does not extend out of the recess.

9. The container according to claim 3 additionally comprising at least one handle disposed on an outer surface of the housing.

10. The container according to claim 3, wherein the housing comprises two portions hinged to each other.

11. The container according to claim 10 additionally comprising a plurality of locks configured to lock the two portions to each other, each of the locks being disposed in a recess of the outer surface of the housing.

12. A container for transporting a pressurized fluid comprising a housing and at least a first pressure vessel disposed within the housing, the housing comprising a first outer surface having a plurality of projections and a second outer surface, opposite the first surface, the second surface comprising a plurality of recesses corresponding to the plurality of projections, the projections and recesses being configured so as to the nestable with each other, and an overpressure sensor connected to the pressure vessel, the sensor having an indicator portion mounted to the housing so as to be visible from exterior of the housing.

13. A transportation container comprising a housing configured to enclose at least one pressure vessel, a first gauge mounted to the housing so as to be visible from a first side of an exterior of the housing, the first gauge configured to indicate a status of the pressure vessel, and a second gauge mounted to the housing so as to be visible from a second side of the exterior of the housing, the second gauge configured to indicate a status of the pressure vessel.

14. The container according to claim 13, wherein the status is an internal pressure of the pressure vessel.

15. The container according to claim 13, wherein at least one of the first and second gauges is disposed in a recess defined on an outer surface of the housing.

16. The container according to claim 13 additionally comprising at least a second pressure vessel disposed within the housing.

17. The container according to claim 16 additionally comprising at least one fluid outlet port disposed on an outer surface of the housing, the outlet port being connected to the first and second pressure vessels so as to receive a pressurized fluid from both the first and second pressure vessels.

18. The container according to claim 17 additionally comprising at least a second fluid outlet port disposed on an outer surface of the housing and connected to the first and second pressure vessels.

19. The container according to claim 18 additionally comprising at least one regulator disposed in line between the pressure vessels in the outlet ports.

20. A transportation unit configured to transport at least one pressure vessel, the unit comprising a housing configured to enclose the at least one pressure vessel therein, the unit also including means for allowing the at least one pressure vessel to discharge a pressurized fluid to an exterior of the housing and for allowing the pressure vessel to be refilled with a pressurized fluid from the exterior of the housing while the housing is enclosed around the pressure vessel.

21. The transportation unit according to claim 20 additionally comprising means for nesting with other transportation units.

22. The transportation unit according to claim 20 additionally comprising means for displaying a status of the pressure vessel on at least two different sides of an exterior of the housing.

23. A method for delivering a pressurized fluid comprising enclosing a pressure vessel within a housing, connecting the pressure vessel with the delivery port disposed on an outer surface of the housing, and mounting a first gauge to a first surface of the housing and a second gauge to a second surface of the housing, the first and second gauges is being configured to display a first data regarding the status of the pressure vessel, the first and second gauges being arranged so as to be visible from two different sides of the housing.

24. The method according to claim 23 additionally comprising connecting a pressure regulator in line between the pressure vessel and the delivery port, the pressure regulator being disposed within the housing.

25. The method according to claim 23 additionally comprising connecting an inlet port to the pressure vessel, the inlet port being disposed on an outer surface of the housing.

26. The method according to claim 23 additionally comprising mounting a handle to the housing.

27. A method for delivering a pressurized fluid comprising enclosing a pressure vessel within a housing, connecting the pressure vessel with the delivery port disposed on an outer surface of the housing, and mounting an overpressure sensor to the housing so as to be visible from an exterior of the housing and connecting the overpressure sensor to the pressure vessel.

28. A portable oxygen delivery system comprising a housing and at least one tank disposed within the housing and configured to store pressurized gaseous oxygen, at least one output port disposed on a first outer surface of the housing, a regulator connecting the tank with the output port such that oxygen from the tank can be discharged through the output port, a plurality of grooves being disposed on a lower surface of the housing and a corresponding plurality of projections disposed on an upper surface of the housing such that when a plurality of housings are stacked on top of each other, corresponding grooves and projections nest with each other thereby stabilizing the stack of housings.

* * * * *